United States Patent [19]

Niermann et al.

[11] Patent Number: 5,354,267
[45] Date of Patent: Oct. 11, 1994

[54] IRRIGATION AND SUCTION APPARATUS

[75] Inventors: Volker Niermann, Garden City, N.Y.; Dennis H. Irlbeck, Jr., Hazlet, N.J.

[73] Assignee: Vital Signs Inc., Totowa, N.J.

[21] Appl. No.: 123,058

[22] Filed: Sep. 20, 1993

[51] Int. Cl.$^5$ .......................... A61M 1/00; A61M 5/00; A61M 16/00
[52] U.S. Cl. ......................... 604/32; 604/35; 604/171; 128/207.14
[58] Field of Search ................ 604/32, 33, 35, 36, 604/118, 119, 171, 248, 265; 128/207.14, 207.16

[56] References Cited

U.S. PATENT DOCUMENTS

| 1,853,202 | 4/1932 | Catlin | 604/32 |
| 3,991,762 | 11/1976 | Radford | 604/119 |
| 4,054,139 | 10/1977 | Crossley | 604/265 |
| 4,342,315 | 8/1982 | Jackson | 604/35 |
| 4,534,542 | 8/1985 | Russo | 604/119 |
| 4,573,965 | 3/1986 | Russo | 604/35 |
| 4,737,148 | 4/1988 | Blake | 604/119 |
| 4,836,199 | 6/1989 | Palmer | 604/171 |
| 4,850,350 | 7/1989 | Jackson | 604/35 |
| 5,277,177 | 1/1994 | Page et al. | 128/207.16 |

*Primary Examiner*—C. Fred Rosenbaum
*Assistant Examiner*—Frank Wilkens, III
*Attorney, Agent, or Firm*—R. Gale Rhodes, Jr.

[57] ABSTRACT

Apparatus for irrigating and suctioning a patient during ventilating wherein in one operation the irrigation fluid is directed solely to the patient and in another operation the irrigation fluid is directed solely to flush the internal lumen of the catheter and in another operation suctioning of the patient is permitted.

17 Claims, 2 Drawing Sheets

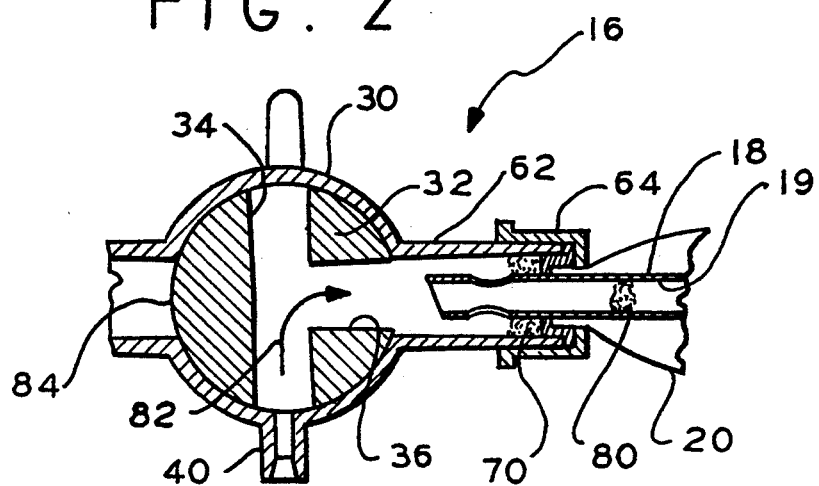
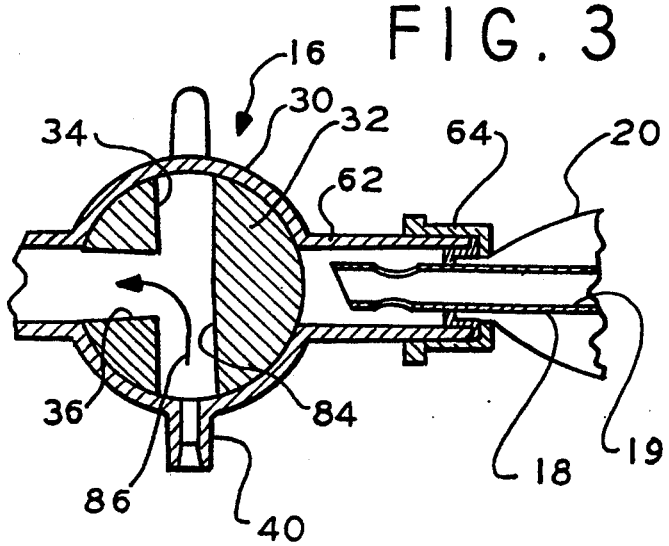
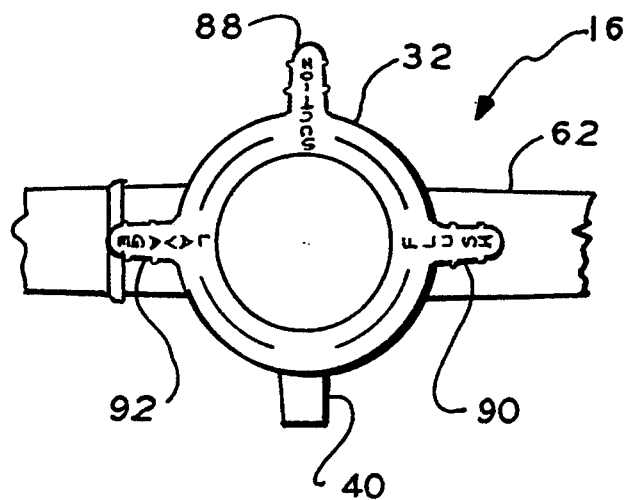

IRRIGATION AND SUCTION APPARATUS

BACKGROUND OF THE INVENTION

This invention relates generally to new and improved irrigation and suction apparatus for use during ventilating of a patient.

More particularly, the present invention is an improvement in the irrigation and suction apparatus disclosed in U.S. Pat. No. 3,991,762 to Radford, U.S. Pat. No. 4,569,344 to Palmer, and U.S. Pat. No. 5,083,561 to Russo. These patents disclose irrigation and suction apparatus for use during patient ventilation wherein the irrigation fluid is introduced, or injected typically under some pressure, into the apparatus and is directed simultaneously to both the trachea and lungs of the patient and to the exterior, and/or internal lumen, of the suction catheter to wash the catheter and to remove or dislodge any materials such as secretions or mucous from the patient's lungs which may have become lodged in the internal lumen of the catheter or lodged in the suction holes at the catheter's tip.

It is believed that it is more effective and therefore preferable for patient irrigation and catheter washing or flushing to introduce the irrigation fluid in one step of operation solely to the trachea and lungs of the patient and solely to the catheter in a second step of operation thereby assuring more positive flow of the irrigation fluid to the patient and catheter in separate steps of operation. Further, a problem associated with surgical suction apparatus of the type disclosed in U.S. Pat. No. 5,083,561 to Russo is that when the irrigation fluid is introduced or injected into the rear portion of the internal lumen of the suction catheter the irrigation fluid flushes or forces any material residing in the internal lumen, such as mucous, back into the patient's trachea and lungs which is undesirable.

Accordingly, there exists a need in the irrigation and suction apparatus art for apparatus which introduces the irrigation fluid in separate steps solely to the patient and solely to the catheter and which irrigation fluid is introduced to the catheter such that any material lodged in the internal lumen of the catheter, such as the above-noted mucous, is flushed away from the patient and not back into the patient's trachea and lungs.

A further problem associated with prior art irrigation and suction apparatus is the escape of ventilation gas from the apparatus in the direction of the catheter and in particular between the catheter and the apparatus surrounding the catheter and through which the catheter is slidably advanced and retracted to suction the patient. A solution to this escaping ventilation gas problem disclosed in U.S. Pat. No. 3,991,792 to Radford is to surround the suction catheter with a conical seal, and the solution taught in U.S. Pat. No. 5,083,561 to Russo is to surround the suction catheter with an O-ring. It is believed that a more effective sealing solution is to provide a normally closed one-way valve in the advancement path travelled by the catheter to suction the patient and which valve automatically fully closes when the suction catheter is withdrawn or retracted past the one-way valve after patient suctioning.

SUMMARY OF THE INVENTION

It is the object of the present invention to satisfy the above-noted needs in the art.

Apparatus embodying the present invention and satisfying the foregoing needs directs irrigation fluid solely to the patient's trachea in one step of operation, in another step of operation directs the irrigation fluid solely to the catheter to flush the internal catheter lumen and to flush or force any material lodged in the lumen, such as mucous, away from the patient, and in another step of operation provides suctioning to the patient. Apparatus embodying the present invention also provides a normally closed one-way valve in the advancement path of the suction catheter and which valve automatically closes when the catheter is retracted to prevent the escape of ventilating gas from the apparatus in the direction of the catheter.

DESCRIPTION OF THE DRAWINGS

FIG. 2 is a partial view of FIG. 1 but showing the three-way stopcock in a second position to provide a passageway for directing irrigation fluid solely to the catheter, particularly the internal lumen of the catheter for flushing;

FIG. 3 is a partial view taken from FIG. 1 but showing the three-way stopcock in a third position to provide a passageway for directing the irrigation fluid solely to the trachea and lungs of the patient; and FIG. 4 is an elevational exterior view of the rear of the three-way stopcock shown in FIG. 1.

DESCRIPTION OF THE PREFERRED EMBODIMENT

Figure 1:
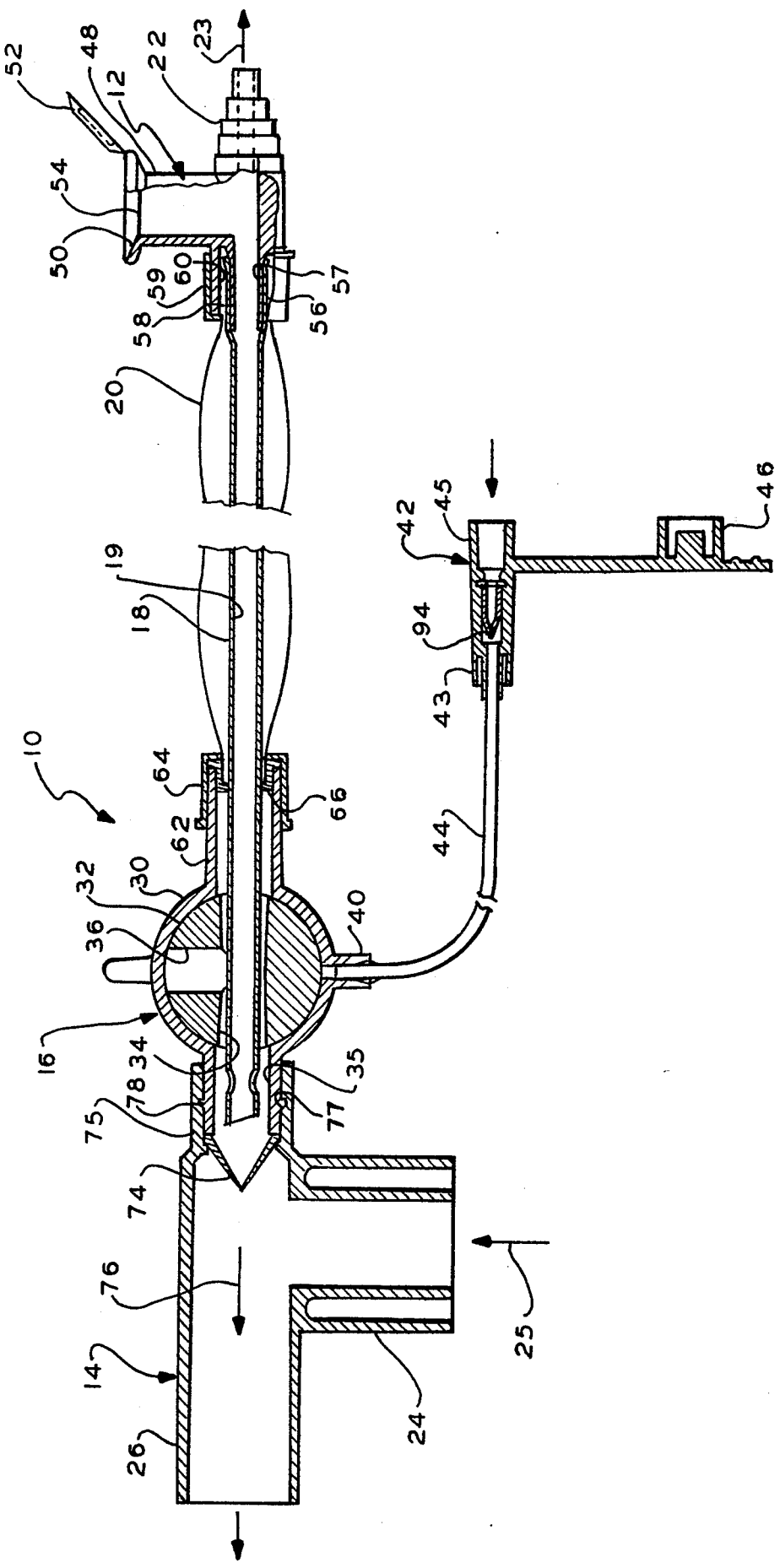
FIG. 1 is a vertical cross-sectional view of the preferred embodiment of irrigation and suction apparatus embodying the present invention; the apparatus in the preferred embodiment includes a three-way stopcock which is shown in a first position to provide a passageway through which the suction catheter is advanced and retracted.

Referring now to FIG. 1, irrigation and suction apparatus embodying the present invention is shown substantially in vertical cross-section and indicated by general numerical designation 10. Apparatus 10 includes a rear coupling indicated by general numerical designation 12, a front coupling indicated by general numerical designation 14, a three-way stopcock or valve indicated by general numerical designation 16, a suction catheter 18 having an internal lumen 19 and an expandable, collapsible protective sleeve 20 substantially surrounding the catheter 18. The rear coupling 12 includes a connector 22 for being connected, such as by tubing, to a suitable source of suction (not shown) of the type known to the art and which suction connection is indicated diagrammatically by the arrow 23. The front coupling 14 is provided with a tubular portion or ventilation gas input port 24 for being suitably connected, in the manner known to the art, to ventilating apparatus (not shown) of the type known to the art for providing ventilating gas to a patient and which connection is indicated diagrammatically by the arrow 25. The front coupling 14 further includes a tubular portion 26 for being suitably connected, in the manner known to the art, to a patient ventilation gas delivery device of the types known to the art such as, for example, a suitable endotracheal tube (not shown).

It will be generally understood that the apparatus 10 of the present invention operates in substantially the same manner as the apparatus disclosed in the above-identified U.S. patents to suction a patient, namely, the suction catheter 18 is advanced through the coupling 14 and through, e.g. an endotracheal tube (not shown) and into the trachea of the patient to suction the trachea and lungs of the patient and remove material such as lung secretions, in particular mucous. As the suction catheter 18 is advanced for suctioning of the patient, the protective sheath 20 collapses and permits the rear portion of the catheter 18 and the rear coupling 12 to be advanced toward the front coupling 14 to extend the suction catheter outwardly and into the trachea of the patient.

Referring now further to the specific structure of the irrigation and suction apparatus 10 of the present invention, it will be understood that the three-way stopcock 16, FIG. 1, includes a generally cylindrical housing 30 in which a disk or disk-like member 32 is mounted rotatably. As may be better understood from FIGS. 2 and 3, the rotatable disk 32 is provided with a generally diametrical passageway 34 extending transversely therethrough and with a generally radial passageway 36 extending partially therethrough and in fluid communication with the passageway 34.

Referring again to FIG. 1, the three-way stopcock housing 30 is provided with an integrally formed irrigation fluid input port 40 and it will be further understood that the apparatus 10 of the present invention may further include an irrigation fluid connector indicated by general numerical designation 42. Connector 42 includes a rearward tubular portion 43 for being connected to the irrigation fluid input port 40, for example, by suitable tubing 44. Connector 42 further includes a forward tubular portion 45 for being suitably connected to a suitable source of irrigation fluid, such as a syringe (not shown) of the type known to the art for introducing or injecting irrigation fluid into the apparatus 10 under pressure. The connector 42 may be provided with an integrally formed closure cap 46 for closing the connector upon the connector being disconnected from the irrigation fluid source.

The rear coupling 12 includes a tubular portion 48 which provides a thumb port 50 for controlling the suction applied to the internal lumen 19 of the catheter 18. The coupling 12 may be provided with an integrally formed closure cap 52 for closing the thumb port 50, if desired, as a barrier for preventing escape of material, e.g. mucous, during suctioning. If desired, the thumb port 50 may be provided with a suitable anti-virile membrane 54, extending transversely thereacross, impervious to air but for preventing the escape of virus from the apparatus 10 through the thumb port 50. The anti-virile membrane 54 may be made of suitable material known to the art for anti-virus protection.

The rearward portion 56 of the suction catheter 18 is mounted, such as by suitable adhesive or a friction fit, to a forward tubular portion 57 formed integrally with the rear coupling 12. The rearward end portion 58 of the protective sleeve 20, which sleeve may be made of a suitable clear or substantially transparent material, is mounted sealingly to the rear coupling 12 by a sealing cap 59 which surrounds and wedgeally engages a tubular member 60 formed integrally with the rear coupling 12. Similarly, the forward end portion of the sleeve 20 is connected sealingly to the rearward tubular portion 62 of the stopcock housing 30 by a sealing cap 64 which surrounds and wedgedly engages an outer portion of the tubular member 62. The three-way stopcock 16 may be provided with a generally annular internal cup seal 66, which may be made of a suitable silicone, and which cup seal 66 slidingly and sealingly engages the outer surface of the suction catheter 18 and removes or scrapes off any material suctioned from the lungs or trachea of the patient, such as mucous, residing on the exterior of the suction catheter 18 as the suction catheter is retracted or withdrawn from the trachea of the patient. Such removed mucous is indicated in FIG. 2 by numerical designation 70.

The three-way stopcock 16, FIG. 1, is mounted to the rear of the front coupling 14 and intermediate the front coupling 14 and the rear coupling 12 by being provided with a forward tubular portion 35 which is received rotatably in the rearward tubular portion 75 of the front coupling. As shown in FIG. 1, the tubular portion 75 is provided with an inwardly extending circular recess 77 which rotatably receives an outwardly extending circular ridge 78 provided on the tubular portion 35; the recess and ridge mount the three-way stopcock 16 to the front coupling 16 and provides a swivel connection therebetween which permits the stopcock 16 to be swiveled axially substantially where the ventilator apparatus connects to the input port 24 which facilitates manipulation of the apparatus 10 by an operator, e.g. physician or nurse, during suctioning or irrigation of the patient.

Referring still to FIG. 1, the irrigation and surgical apparatus 10 of the present invention may further include a one-way duckbill valve 74 mounted internally of the front coupling 14 by being suitably secured, such as by suitable adhesive, to the interior of the tubular portion 75 of the front coupling 14. From FIG. 1 it will be noted that the one-way duckbill valve 74 is mounted internally of the front coupling 14 intermediate the ventilating gas input port 24 and the three-way stopcock 16. Thus, upon the suction catheter 18 being retracted into the position shown in FIG. 1 or further retracted into the positions shown in FIGS. 2 and 3, it will be understood that the one-way duckbill valve 74 closes automatically and prevents ventilating gas entering the ventilating gas input port 24 from escaping from the front coupling 14 towards the three-way stopcock 16 and therethrough to the protective sleeve 20 or to the atmosphere or to the suction source. The advancement path along which the suction catheter 18 advances for suctioning the patient as generally described above is indicated in FIG. 1 by the arrow 76 and it will be understood that as the suction catheter 18 is advanced through the coupling 14 for insertion into the patient's trachea as described above, the front end of the catheter 18 engages the normally closed one-way duckbill valve 74 and opens the valve permitting the suction catheter to pass therethrough, and upon the suction catheter 18 being retracted as shown in FIG. 1 and further retracted as shown in FIGS. 2 and 3 for irrigation, it will be understood that the duckbill valve 74 automatically closes and prevents the escape of ventilating gas in the direction of the catheter 18 and stopcock 32 as described above and reduces the dead space of the ventilating gas.

The irrigation fluid connector 42, FIG. 1, may also be provided with an internal, normally closed, one-way duckbill valve 94 for preventing material, such as mucous, from the lungs of the patient, or exhalation gas from the patient, from escaping to the atmosphere upon the cap 42 not being closed to the rearward portion 45 of the connector. Such escaping material and gas could expose attending personnel, such as physicians and nurses, to any virus or bacteria contained in such material or patient exhalation gas. The normally closed valve 94 is opened in response to the irrigation fluid acting thereagainst to permit the irrigation to pass therethrough and upon cessation of flow therethrough of the irrigation fluid the valve 94 closes automatically.

Referring now particularly to the operation of the irrigation and suction apparatus 10 of the present invention, upon the stopcock disk 32 being rotated into the position shown in FIG. 1, the passageway 34 provides a passageway through which the suction catheter 18 is advanced for insertion through the front coupling 14 and into the trachea of the patient to suction the patient and through which passageway 34 the suction catheter 10 is retracted for irrigation, the retracted positions of the catheter for irrigation being shown in FIGS. 2 and 3.

Upon the rotatable disk 32 of the three-way stopcock 16 being rotated into the position shown in FIG. 2, and upon the connector 42, FIG. 1, being connected to the above-described suitable source of irrigation fluid not shown and such irrigation fluid being introduced or injected under pressure to the irrigation fluid input port 40, the passageways 34 and 36 cooperate to provide a passageway for directing the irrigation fluid solely to the catheter 18 to wash or flush the internal catheter lumen 19 and dislodge or remove any material removed from the lungs and trachea of the patient such as the mucous indicated by numerical designation 80 in FIG. 2; the flow of such irrigation fluid is indicated by the curved arrow 82 in FIG. 2. It will be understood that the solid portion 84 of the rotatable disk 32 is blocking the irrigation fluid from being directed simultaneously to the trachea of the patient. It will be further understood from FIG. 2 that upon the irrigation fluid entering the internal lumen 19 of the suction catheter 18 material residing or lodged therein, such as mucous 80, is washed or flushed away from the patient and through the internal lumen to the suction apparatus described above.

Upon the rotatable disk 32 of the three-way stopcock 16 being rotated into the position shown in FIG. 3, the passageways 34 and 36 cooperatively provide a passageway for directing irrigation fluid entering the port 40 solely to the trachea of the patient as indicated by the curved arrow 86 indicating such flow path of the irrigation fluid. The irrigation fluid, as will be understood from FIG. 1, exits the three-way stopcock 16, flows through she front coupling 14 into the trachea and lungs of the patient through the above-described, but not shown, endotracheal tube which may be connected to the front coupling 14 as described above. It will be noted that in the position shown in FIG. 3, the solid portion 84 of the rotatable disk 32 blocks the irrigation fluid entering the port 40 from being directed to and entering the internal lumen 19 of the suction catheter 18.

Accordingly, it will be understood that the three-way stopcock 16 given its three positions described above, may be considered to be a suction control valve, an irrigation control valve, a valve for controlling flushing of the internal lumen of a catheter, or a combination valve for such functions.

Referring now to FIG. 4, the rotatable disk 32 of the three-way stopcock 16 extends outwardly of the stopcock housing 30 and may be provided with outwardly extending rotation members or levers 88, 90 and 92 which may be suitably marked, such as by embossing, to indicate the suction, catheter flush and patient irrigation or lavage positions for the disk 32 shown respectively in FIGS. 1, 2 and 3. The three-way stopcock 16 may be provided with a suitable marker or registration indication, not shown, with which the members 88, 90 and 92 may be aligned to assure that the stopcock disk 32 is properly rotated into the desired position for suctioning, catheter flushing or patient irrigation or lavaging.

It will be understood by those skilled in the art that the terms suction and suction apparatus as used herein are sometimes referred to in the art as aspiration or aspirating apparatus and that the term irrigation fluid is sometimes referred to in the art as a lavage fluid and the act of patient irrigating is sometimes referred to in the art as lavaging of the patient.

The irrigation and surgical apparatus 10 of the present invention may be provided with a suitable antimicrobial coating of the types known to the art, such as for example silver zealites. More particularly, such antimicrobial coating may be applied to the interior of the suction catheter 18, the interior of the protective sleeve 20, or the interiors of the front and rear couplings 12 and 14 and to the interior of the three-way stopcock housing 32.

It will be understood that many variations and modifications may be made in the present invention without departing from the spirit and the scope thereof.

What is claimed is:

1. Irrigation and suction apparatus, comprising:
   a catheter for suctioning of a patient, said catheter having an internal lumen and first and second end portions, said first end portion for being connected to suction apparatus to suction said patient; and
   valve means mounted proximate said second end portion of said catheter, said valve means provided with an input port for receiving irrigation fluid and said valve means having at least three positions, said first position providing a passageway through which said second portion of said catheter may be extended for insertion into said trachea to suction said patient and through which at least said catheter can be retracted for irrigation of said patient, said second position providing a passageway for directing said irrigation fluid solely to the trachea of said patient and said third position providing a passageway for directing said irrigation fluid solely to said second end portion of said catheter to flush said internal lumen.

2. Irrigation and suction apparatus for suctioning material such as mucous from the trachea of a patient during ventilation, comprising:
   a catheter having an internal lumen and opposed first and second end portions;
   first and second couplings, said first end portion of said catheter mounted to said first coupling and said first coupling for communicating a source of suction with said internal lumen of said catheter, and said second coupling for communicating ventilating apparatus with the trachea of said patient;
   stopcock means mounted to said second coupling intermediate said second coupling and said first coupling, said stopcock means having an irrigation fluid input port for receiving irrigation fluid and having at least first, second and third positions, said first position providing a passageway through which said catheter is advanced for insertion through said second coupling and into said trachea of said patient to suction said patient and through which said catheter is retracted for irrigation, said second position providing a passageway for directing said irrigation fluid solely to the trachea of said patient to irrigate said trachea, and said third position providing a passageway for directing said irrigation fluid solely to said catheter to flush said internal lumen.

3. The apparatus according to claim 2 wherein said apparatus further includes a normally closed one-way valve mounted internally of said second coupling in advance of said stopcock means and for preventing ventilating gas from said ventilating apparatus from escaping through said stopcock means while said stopcock means is in said first position and said catheter is retracted.

4. The apparatus according to claim 3 wherein said one-way valve is a duckbill valve.

5. The apparatus according to claim 2 wherein said second coupling is provided with a ventilating gas input port for connection to said ventilating apparatus and wherein said apparatus further includes a normally closed one-way valve provided internally of said second coupling intermediate said ventilating gas input port and said stopcock means, said one-way valve engageable by said catheter to open said valve and permit said catheter to be inserted therethrough upon said catheter being inserted into said trachea of said patient, said normally closed valve preventing ventilating gas from said ventilating means from escaping through said stopcock means and being diverted from said patient while said catheter is not inserted through said one-way valve.

6. The apparatus according to claim 5 wherein said one-way valve is a duckbill valve.

7. The apparatus according to claim 2 wherein said apparatus further comprises an expandable, collapsible sleeve normally enclosing said catheter and having opposed first and second end portions sealingly mounted to said first and second couplings.

8. The apparatus according to claim 2 wherein said stopcock means further comprises an internal seal slidably engaging the exterior of said catheter and for preventing material residing on said exterior of said catheter from escaping through said stopcock means and into the atmosphere.

9. The apparatus according to claim 2 wherein said apparatus further includes an irrigation fluid connector for residing intermediate said irrigation fluid inlet port and a source of irrigation fluid, said connector provided with an internal, normally closed, one-way valve engageable and opened by said irrigation fluid and normally closed to prevent said material from escaping through said connector into the atmosphere upon said stopcock means being in said second position and said connector not being connected to said source of irrigation fluid.

10. The apparatus according to claim 9 wherein said connector is provided with an input port for being connected to said source of irrigation fluid and wherein said connector is provided with an integrally formed protective cap for closing said input port while said connector is not connected to said source of irrigation fluid.

11. The apparatus according to claim 2 wherein said first coupling is provided with a thumb port apparatus providing an opening for controlling suction communicated to said catheter and wherein said apparatus further comprises an anti-virile membrane mounted transversely in said apparatus below said openings.

12. The apparatus according to claim 11 wherein said thumb port is provided with an integrally formed protective cap for closing said opening.

13. The apparatus according to claim 2 wherein the interior of said catheter is provided with a predetermined antimicrobial coating.

14. The apparatus according to claim 13 wherein the interior of said first and second couplings is provided with a predetermined antimicrobial coating.

15. The apparatus according to claim 7 wherein the interior of said protective sleeve is provided with a predetermined antimicrobial coating.

16. The apparatus according to claim 2 wherein said stopcock means is mounted to said second coupling in a swivel connection to facilitate manipulation of said apparatus during said irrigation and suction of said patient.

17. Suction apparatus for use during ventilation of a patient, comprising:
   means for applying suction to said patient;
   means for controlling the suction applied to said patient;
   means for connecting said apparatus to a source of ventilating gas; and
   means permitting said means for connecting said apparatus to a source of ventilating gas to be swiveled axially with respect to said means for applying suction to said patient at substantially the point at which said source of ventilating gas is connected to said apparatus.

* * * * *